(12) United States Patent
Flanagan et al.

(10) Patent No.: US 6,453,608 B1
(45) Date of Patent: Sep. 24, 2002

(54) GELLAN GUM SEED COATING

(75) Inventors: John Flanagan, Neshanic Station, NJ (US); Helen Anderson, St. Charles, MO (US); Frank Miskiel; You-Lung Chen, both of San Diego, CA (US)

(73) Assignee: Monsanto Company, St. Louis, MO (US)

( * ) Notice: Subject to any disclaimer, the term of this patent is extended or adjusted under 35 U.S.C. 154(b) by 0 days.

(21) Appl. No.: 09/301,988

(22) Filed: Apr. 29, 1999

Related U.S. Application Data

(63) Continuation-in-part of application No. PCT/US98/23430, filed on Oct. 30, 1998.
(60) Provisional application No. 60/064,454, filed on Oct. 31, 1997.

(51) Int. Cl.7 .................................................. A01C 1/06
(52) U.S. Cl. ..................................................... 47/57.6
(58) Field of Search ................................. 47/57.6, 58.1

(56) References Cited

U.S. PATENT DOCUMENTS

| | | | | |
|---|---|---|---|---|
| 4,272,417 A | * | 6/1981 | Barke et al. | 47/57.6 |
| 4,503,084 A | * | 3/1985 | Baird et al. | 426/573 |
| 4,517,216 A | * | 5/1985 | Shim | 426/573 |
| 4,769,945 A | * | 9/1988 | Motoyama et al. | 47/57.6 |
| 4,780,987 A | | 11/1988 | Charles et al. | 47/57.6 |
| 4,881,343 A | * | 11/1989 | Sannan et al. | 47/57.6 |
| 5,112,445 A | * | 5/1992 | Winston, Jr. et al. | 162/178 |
| 5,230,853 A | * | 7/1993 | Colegrove et al. | 264/186 |
| 5,580,975 A | * | 12/1996 | Tada | 536/123 |
| 5,585,127 A | * | 12/1996 | Freeport et al. | 426/93 |
| 5,688,543 A | * | 11/1997 | Freeport et al. | 426/93 |
| 5,731,204 A | * | 3/1998 | Rutter et al. | 435/430.1 |
| 5,750,166 A | * | 5/1998 | Schellhaass | |
| 5,827,707 A | * | 10/1998 | Lamberti | 435/178 |
| 5,858,746 A | | 1/1999 | Hubbell et al. | 435/177 |
| 2002/0011025 A1 | * | 1/2002 | Kohno et al. | 47/57.6 |

FOREIGN PATENT DOCUMENTS

| | | | |
|---|---|---|---|
| EP | 0 048 123 | * | 3/1982 |
| EP | 0 454 373 A2 | * | 10/1991 |
| JP | 403022934 A | * | 1/1991 |
| JP | 409074898 A | * | 3/1997 |
| JP | 409194282 A | * | 7/1997 |
| JP | 410014423 A | * | 1/1998 |
| JP | 410191725 A | * | 7/1998 |
| WO | WO009636727 A1 | * | 11/1996 |
| WO | WO 98 27151 A | | 6/1998 |
| WO | WO 99/22769 | * | 5/1999 |

OTHER PUBLICATIONS

Research Disclosure, GB, Industrial Opportunities Ltd. Havant, "Use of Gellan Gum To Prepare Gels That Can Be Dried And Subsequently Rehydrafted To Their Original Shape", No. 345, p. 42 XP000336554, dated Jan. 1, 1993.
Research Disclosure, GB, Industrial Opportunities Ltd. Havent, "Simple Films and Coatings Made With Gellan Gum", No. 361, p. 244 XP000453954, dated May 1, 1994.
Research Disclosure, GB, Industrial Opportunities Ltd. Havent, "Gellan Gum Coating And Adhesion Systems", No. 350, p. 418 XP000373023, dated Jun. 1, 1993.
Whistler R. L. Et al. (ED.): "Industrial Gums. Polysaccharides And Their Derivatives", 3rd Edition, pp. 371–380 XP002132492, dated 1994.
PCT/US99/23987 Search Report dated Apr. 5, 2000.

\* cited by examiner

*Primary Examiner*—Peter M. Poon
*Assistant Examiner*—Jeffrey L. Gellner
(74) *Attorney, Agent, or Firm*—Banner & Witcoff LLP

(57) ABSTRACT

A seed coating comprising gellan gum is disclosed along with a process which comprises admixing gellan gum and water under effective shear conditions to prepare an aqueous gellan gum coating composition thereof whereby the aqueous gellan gum coating composition may be applied in an adherent fashion to a seed to form a gellan gum coated seed. A gellan gum seed coating composition may indicate one or more bioactive(s) and optionally one or more colors.

16 Claims, 1 Drawing Sheet

UTC and 1.5% gellan
E = 10 mls

GELLAN GUM SEED COATING

This is a Continuation-In-Part of pending International Application No. PCT/US98/23430 having an International Filing Date of Oct. 30, 1998 which claims the benefit of provisional application Ser. No. 60/064,454 filed on Oct. 31, 1997.

FIELD OF THE INVENTION

This invention relates generally to seed coating(s) and to a method to prepare compositions useful to coat a seed.

More particularly this invention relates to a seed coated with gellan gum, use of gellan gum as a seed coating, a method to prepare a gellan gum composition useful to coat a seed, a gellan gum composition useful to coat a seed(s), and to a method for coating a seed(s) with gellan gum. If desired one or more bioactives or colors may be employed with or in the seed coating of this invention.

BACKGROUND OF THE INVENTION

The application of a material to a seed is practiced in the agricultural industry. Identification of seed type or age is often accomplished through the application of a suitable dye or pigment to the seed. Growth and vigor of seed can be enhanced by the addition of nutrients or growth enhancers to the seed. Sometimes such additions can be used to provide a more consistent size and shape to achieve better performance in planting equipment.

The current direction of the agricultural chemical industry is focused on more targeted methods for the delivery of biologically active products. In addition the ongoing genetic engineering revolution has resulted in much higher value conveyed to the seed. To both protect the seed value and identify the genetic traits of the seed, seed coating offers the best accepted method to resolve these issues.

Even with the foregoing and other seed coating compositions, the agriculture industry continues to desire an enhanced seed coating. A process of preparing such an enhanced seed coating economically and efficiently, continues to be of interest.

OBJECTS OF THE INVENTION

It is an objective of this invention to provide a seed coated with gellan gum and optionally with one or more colors or bioactives.

It is further objective of this invention to provide a process for using gellan gum as a seed coating.

It is another objective of this invention to provide a seed coating comprising gellan gum.

It is an additional objective of this invention to provide a process for preparing a gellan gum composition useful for coating seeds.

It is yet a further objective of this invention to provide a gellan gum composition useful to coat a seed.

It is yet another objective of this invention to provide a process for preparing a coated seed wherein the coating is selected from gellan gum, gellan gum and a color and gellan gum and optionally one or more bioactive(s) and optionally a color.

The above objectives and other objectives are met in this invention which is more particularly described hereinafter without limitation.

BRIEF SUMMARY OF THE INVENTION

In one embodiment, this invention comprises a seed coating comprising gellan gum.

In another embodiment, this invention further comprises a seed coated with gellan gum.

In another embodiment this invention comprises a process for preparing a gellan gum composition useful for coating a seed, which comprises the steps of admixing gellan gum and water under effective shear conditions with and without heating and with or without an acceptable sequestrant to prepare an aqueous gellan gum coating composition thereof. If desired, a color and/or one or more bioactive(s) may be employed in a composition and process of this invention.

In another embodiment this invention further comprises preparing the aforementioned aqueous gellan gum coating composition and applying the same in an acceptable adherent fashion to a seed(s) whereby a gellan gum coated seed is formed.

Other embodiments of this invention are included herein. These above and other embodiments are described in more detail hereinafter.

DETAILED DESCRIPTION OF THE INVENTION

Figure 1:
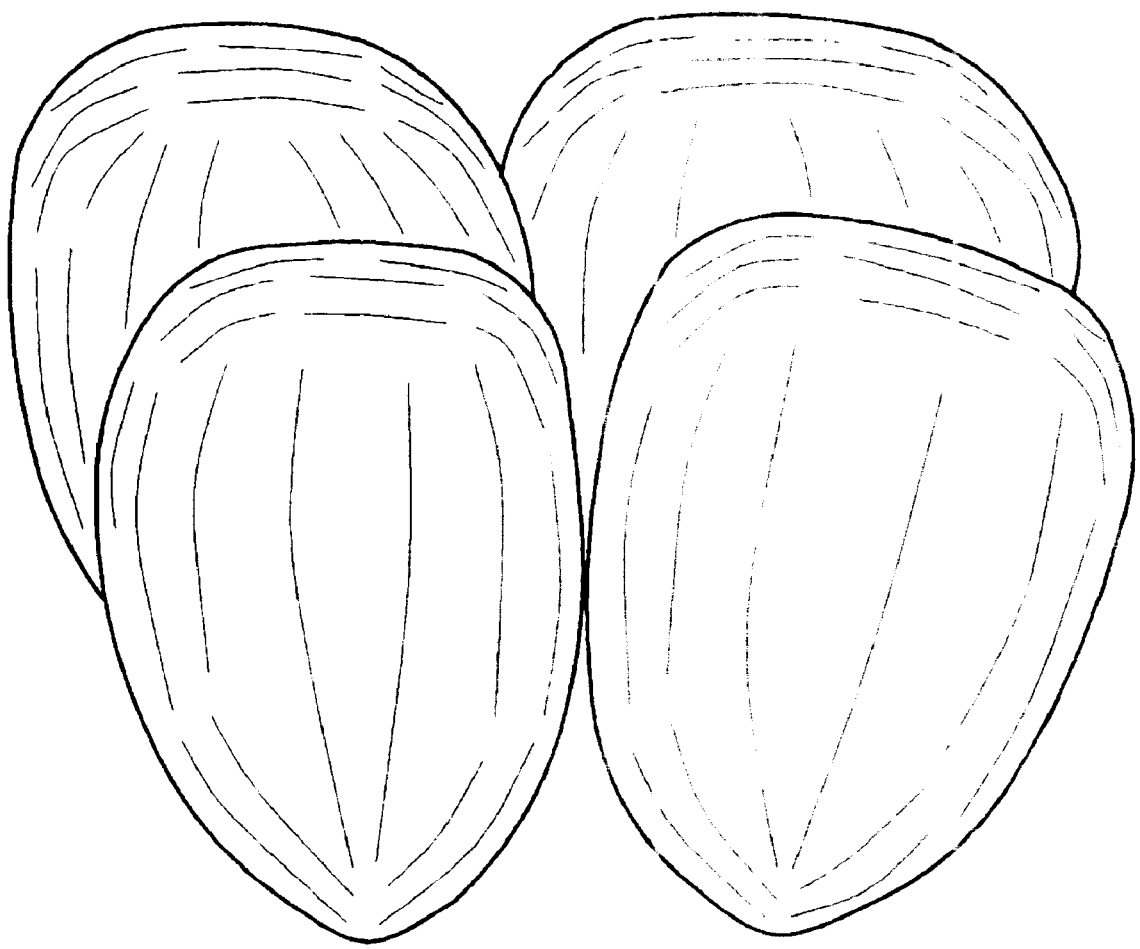
FIG. 1 shows a corn seed coated in accordance with this invention.

Gellan gum useful herein is produced by inoculating a carefully formulated fermentation medium with the microorganism Sphingamonas elodea (ATTC 31461, American Type Culture Collection, 10801 Unity Boulevard, Manassas, Va. 20110). Gellan gum is available from Monsanto Company, 800 North Lindbergh Boulevard, St. Louis, Mo. 63167, USA. Typical brand names include KELCOGEL® and GELRITE®. Gellan gum useful herein includes any available form such as but not limited to, non-clarified, clarified, and partially-clarified native, deacetylated and partially deacetylated forms as well as mixtures thereof and the like. Kelcogel® and Gelrite® are registered trademarks of and are available from Monsanto Company. Gellan gum may be prepared according to the methods disclosed in U.S. Pat. Nos. 4,326,052 and 4,385,123. Both of these patents are incorporated herein their entirety by reference.

Optional components of the gellan gum aqueous coating composition of this invention may include but are not limited to one or more bioactives, a color additive(s) and/or other coating polymers as will be readily apparent to those of skill in the art in particular after reading this specification. A typical useful plasticizer is propylene glycol although any equivalent or substantially equivalent plasticizer may be satisfactorily employed herein if desired.

The scope and utility of the present invention is not limited to any bioactive. Bioactives which may be effectively employed as a coating in this invention are not limited and include those such as pesticides, herbicides, fungicides, insecticides, and the like, mixtures thereof and the like. An effective amount of such one or more bioactives can be employed. Illustrative herbicides useful herein, include but are not limited to, glyphosate and its water soluble salts and derivatives including but not limited to those disclosed in U.S. Pat. No. 3,799,758 which issued to John E. Franz on Mar. 26, 1974, which is incorporated herein by reference in its entirety.

The process for preparing a coated seed according to this invention preferably comprises admixing gellan gum and water under effective shear, heat and ionic conditions to prepare an aqueous gellan gum coating composition and applying the aqueous gellan gum coating composition in an effective fashion to a seed whereby a coated seed is formed. A drying step typically occurs and typically follows.

The aqueous gellan gum coating composition useful to coat seeds is preferably admixed in any suitable container or the like prior to applying the gellan gum composition to or on a seed to be coated. Initially the gellan gum and water are admixed and further mixing is carried out under effective shear to form an aqueous seed coating composition. Typically the gellan gum coating aqueous composition prior to application of such effective shear will have a viscosity in the range from about 44 cps. to about 55,500 cps. and preferably from about 2200 to about 50,000 cps although gellan gum compositions having greater and lesser viscosities may sometimes be employed depending on a number of factors.

If desired, gellan gum compositions comprising gellan gum and/or gellan gum and one or more of a another ingredient such as a polymer such as, but not limited to, those selected from the group consisting of hydroxypropyl cellulose, hydroxypropyl methyl cellulose, sodium carboxymethyl cellulose, sugar, aspartame, maltodextrin, tapioca dextrin, modified food starches, polyvinylpyrolidone, mixtures thereof and the like may be employed in this invention. As employed herein, the term "gellan gum" includes and is not limited to gellan gum and/or compositions of gellan gum with one or more of these polymers or a sugar.

The aqueous gellan gum composition of this invention may be mixed in or by any suitable mixing system preferably until complete or substantially complete mixing has been accomplished. Some heating may be necessary to achieve dispersion and hydration of gellan gum. The amount of shear preferably employed is an effective amount, i.e., preferably that which produces a well mixed homogenous gellan gum composition. The aforementioned admixing can be carried out by any convenient means including but not limited to use of a propeller or stirrer system although generally stirring by a convenient mechanical means is acceptable. Other convenient forms of mixing can be employed.

Optionally, if desired, various other ingredients may be employed in the gellan gum aqueous composition include any ingredient which is compatible or can be made compatible with an aqueous gellan gum composition useful to coat seeds of this invention, (such as, but not limited to, colors, color system(s), flavor(s), sweetener(s), mint(s), fragrance(s), plasticizer(s), clays, diatomacious earth, and mixtures thereof and the like).

The gellan gum aqueous composition is preferably applied to the seed(s) to be coated in a batch, semi-continuous or continuous process or some combination thereof in a manner which produces a satisfactorily uniformly coated seed. The gellan gum composition may be applied to seeds to be coated using any satisfactory application and drying system or combination of some application system and some drying system. The combination is not critical nor is the arrangement of equipment to carry out this invention.

The amount of gellan gum in the gellan gum aqueous composition useful for coating seeds of this invention is an effective amount which is generally from about 0.1% to about 10% and preferably from about 0.25% to about 5% by weight gellan gum of the total gellan gum aqueous composition although greater and lesser amounts of gellan gum may be employed if desired. A most preferred range is about 0.75% to about 2%.

During application of the gellan gum aqueous composition to the seed to be coated, the temperature of the gellan gum aqueous composition is preferably in the range from about 25° C. to about 45° C. although greater or lesser temperatures may be employed if desired. It is preferred that the gellan gum composition be maintained in a solution or dispersion or an applicable state during its coating application to the seed(s) to carry out this invention.

Historically those of skill in the art have considered a composition having a viscosity of about 1,000 centipoise (cps) as being at the upper bound as regards usefulness as a coating composition due to that high viscosity. Since an aqueous composition comprising gellan gum (about 1.8% by weight gellan gum) and water has a viscosity of about 28,460 cps at a temperature of about 30° C., those of skill in the art would not have considered such a composition useful to coat seeds and would have been steered away from it for this invention. Now, however, the inventors have surprisingly discovered that despite the high viscosity of a gellan gum composition at room temperature that such compositions are very useful to coat seeds as the invention herein provides.

Gellan gum may be coated onto these seeds which are initially uncoated (i.e. have their natural outer coating) or are those seeds which have been coated with one or more prior coatings (overcoating) of an acceptable coating composition which allows adherency with gellan gum. An initial coating may comprise one or more polymers such as cellulosics, dextrins, acrylics, any colors or other industry acceptable coating material. A gellan gum composition may be employed as a primary coating on a seed, as a secondary coating on a seed, or as a tertiary coating if desired. One or more coating applications of gellan gum may be made to a coated or uncoated. seed in accordance with this invention, although typically one or two coatings are effective and are preferred. If desired, a gellan gum coating may be applied to a seed in accordance with the invention in an instance wherein a protective coating is desired, for example to protect coated or uncoated seed from possible physical damage. In one embodiment a gellan gum coating may be the only coating and may comprise a first coating or a second or a third coating. The coating of this invention may be applied to a seed(s) in layers if desired or any fashion so as to provide the benefits of this invention.

Typically the amount of gellan gum which is coated onto a seed in practicing this invention is that amount which provides a gellan gum coated seed having a weight gain (during coating) from about 0.025% to about 10% weight percent of the total seed weight and preferably from about 0.05% to about 5% weight percent of the total seed weight although larger and smaller weight percents may be employed if desired. Typically this amount of gellan gum is that amount which is necessary to provide an effective or desired coating. The amount of a bioactive employed herewith is preferably a bioactive effective amount which will depend to a large degree upon the bioactive(s) employed and the use conditions.

Neither the seed shape nor the seed size are critical. Preferable sizes of seeds include but are not limited to those seeds which are about ¼ inch to about one inch in size and weigh about 100 mg. to 0.1 grams each although seeds may be employed which are larger or smaller in size and of lighter and heavier weight if desired. Preferred shapes are round or oval; however, other and any shape may be employed if desired.

Seeds useful herein include all seeds and are not limited to a particular seed or seeds.

Illustrative colors and colorants useful herein include without limitation, pigments, dyes, lakes, natural colors, and oxides (including titanium dioxide) and the like, may be optionally employed with gellan gum used in practicing this invention. The gellan gum aqueous composition may optionally contain a suitable color or colorants for application to a colored or noncolored coated or uncoated seed.

Seeds to be coated according to this invention may be colored, neutral or have their natural color or may be absent color. If one of more colors, dyes, lakes, or pigments or mixtures thereof are employed in a gellan gum coating composition herein, such as for example, an FDA certified color, dye, lake, natural colors, or pigment, the color or combination of colors is not critical and may be selected by those of skill in the art based upon a need at the time of the coating operation. Examples of suitable pigments which are useful in this invention include, without limitation, FD&C and D&C lakes, titanium dioxide, magnesium carbonate, talc, pyrogenic silica, iron oxides, channel black, insoluble dyes and mixtures thereof and the like. Also, natural pigments such as riboflavin, natural colors, carmine 40, curcumin, annatto, mixtures thereof and the like are acceptable herein. Other examples of pigments suitable herein include, without limitation, these disclosed in Jeffries U.S. Pat. No. 3,149,040 and Butler et al., U.S. Pat. No. 3,297,535, as well as in Colorcon U.S. Pat. No. 3,981,984. These three patents are incorporated herein by reference in their entirety. In the absence of a colorant, the gellan gum composition typically produces a clear or substantially clear coating on a coated seed.

As employed herein, the term "adherent" means that the gellan gum coating effectively adheres to the coated seed until an appropriate use.

Reference is made to PCT International Application No. PCT/US98/23430 having an International Filing Date of Oct. 30, 1998, which relates to Gellan Gum Tablet Coating.

Although the gellan gum coating composition of this invention will initially be an aqueous composition, the seed coating will preferably be dried or substantially dried prior to, upon its exit or removal from the coating application system or at sometime in preparing coated seeds. The coated seeds may be placed in suitable packaging if desired.

The amount of coating provided to the surface of the seed is an effective amount from a coating perspective and it is that amount which provides at least a minimum effective coverage of the surface area of the seed, although this invention also encompasses those instances where there is partial coverage of the exterior surface as well.

If desired, one or more layers of gellan gum coating may be employed using this invention. Those of skill in the art will be able to determine the extent of any layering depends somewhat on the seed selected and its physical and chemical and properties and characteristics from a reading of this specification and using their skill in the art.

It is preferred that coating be continuous or nearly continuous and over the surface of the seed. An effective depth of coating is provided. It is also desired that the seed coatings herein be somewhat resilient with respect to handling, to peeling and to flaking and being rubbed off of the coated seed.

As referred to above, application of the gellan gum aqueous composition as a coating to the seed is preferably carried out by placing a seed capable of receiving and adhering a gellan gum seed coating composition of this invention in any acceptable coating application system. An acceptable coating application system is illustratively any system which has the capability to apply a gellan gum coating composition of this invention to a seed to provide an effectively, preferably uniformly coated seed.

Air Suspension Coating systems useful here as an illustrative application system include those described in Ullman's Encyclopedia of Industrial Chemicals, Volume A16 pages 583–584 (1990) which includes a description of the Wurster process. Ullman's Encyclopedia of Industrial Chemicals, Volume A16 pages 583–584 (1990–1996) is incorporated herein by reference in its entirety. This incorporation includes the chapter Microencapsulation authored by Christopher A. Finch of Pentafin Associates, Weston Turville, AYLESBURY HP 22 5TT, UK.

Also, acceptable for use to prepare coated seeds of this invention are illustratively a variety of side vented coating pans, spray dryer(s), continuous coating pans, and conventional coating pans, such as those with systems for mechanically providing the gellan gum composition to a seed in an effective manner using mechanical means as for example by spray nozzles or the like. Also acceptable as a spray tower system is a conventional fluid bed tower equipped with a suitable spray apparatus. Any application system capable of applying a composition of this invention to a seed is an acceptable system for coating seeds employing the aqueous gellan gum coating composition of this invention. As the coating system is not critical, any size coating system is acceptable. Batch and continuous processes, semi-continuous and suitable variations thereof are envisioned without limitation.

If desired, the same or a similar coating application system can be employed for both a first and a second or sequential coating applications or different coating application systems may be employed for a first or second or more coating applications. If desired, the same coating application system can be used to apply a first and second or more coatings with or without removal of the seeds from such a system between the first and second or more coatings.

While illustrative useful application systems have been described herein, those of skill in the art will recognize that such description is provided to provide information as to the possible application and use herein in accordance with this invention. Those of skill in the art will recognize that the actual operation of any such application system will vary and may be varied from a text book type description of such operation in according with the parameters and conditions of any desired operation, among other factors. Configuration and design changes may be made on such applications systems and operating parameters may be varied to produce an effective result.

EXAMPLES

Examples 1–9, are provided to illustrate the preparation of acceptable coated seeds in accordance with this invention and are provided by way of illustration and are not intended to limit the invention in any way. All percents and any parts are by weight unless otherwise indicated.

Example 1

Gellan Gum Coating Applied on Corn Seed (Maize Seed)

In this example a clear coat of gellan gum solution was applied to corn seed (kernels).
Procedure: Prepare and use a 1.5% Gellan gum solution:

A gellan gum composition useful for coating seeds was prepared comprising about 30 grams gellan gum, about 1,968 grams water and about two grams sodium citrate to provide a 1.5% by weight gellan gum aqueous composition useful for coating seeds.

The aqueous gellan gum composition was prepared by weighing the water into a clean dry residue-free beaker and weighing out the gellan gum (Kelcogel) and sodium citrate. The water was then mixed with a laboratory mixer to create a vortex. The gellan gum powder and sodium citrate was slowly introduced into the vortex to achieve dispersion. Stirring was continued without heat to finalize the dispersion of gellan gum. Heat was applied while stirring until the dispersion temperature was about 70° C. to hydrate the gellan gum. Care was taken to avoid charring the resulting composition, i.e. employing sufficient stirring and avoiding overheating. The beaker was removed from the stir plate and cooled to ambient temperature to make the gellan gum aqueous composition available for coating.

Seed Coating Procedure:

Fifty grams of a selected (commercial fertile) seed type, such as corn or soybean, is weighed and poured into a 200 c.c. glass or plastic bottle container. The bottle is placed between two rotating rollers and is rotated at a speed of about 60 rpm. This rotation is initiated just prior to addition of gellan gum described hereafter.

In a first addition part, an initial 2 c.c. of the above-described gellan coating solution is drawn into a syringe and the coating solution is applied by the syringe to the inside walls of the rotating bottle through a syringe accessible end of the rotating bottle. The coating solution is thence applied evenly to 50 grams of corn seed inside the rotating bottle.

After this applied coating solution is applied, the bottle is picked up by hand from the rollers and shaken for about 2 to about 5 seconds or so or tapped on by finger for a few seconds, permitting the applied solution to be evenly spread inside the bottle and to prevent the seeds from sticking to the wet walls of the bottle. The bottle is placed back between rollers and is rotated at about 60 rpm for an additional about 2 to about 5 minutes. Thus the coating solution is coated on the seed surface.

After the applied coating in the immediate above step visually appears dry or somewhat dry, an additional 2 c.c. of the above-identified gellan gum solution is applied to the same 50 grams of corn seed by the aforedescribed syringe technique into the syringe accessible end of the rotating bottle. This brings the total gellan gum solution applied to about 4 c.c.

Again after this applied coating solution is applied, the bottle is then picked up by hand and shaken for about 2 to about 5 seconds or so or tapped on by finger for a few seconds, permitting the applied solution to be evenly spread inside the bottle and to prevent the seeds from sticking to the wet walls of the bottle. The bottle is placed back between rollers and is rotated at about 60 rpm for an additional about 2 to about 5 minutes. The gellan gum coating solution is thereby evenly coated on the seed surface. This resulted in a clear coating.

After the applied coating above step visually appears dry or somewhat dry, an additional 2 c.c. gellan solution is applied to the same 50 grams of corn seed by use of the syringe technique. This makes a total (at this point in the process) of 6 cc of gellan gum solution applied.

After this applied coating solution is applied, the bottle is then picked up by hand from the rollers and shaken for about 2 to about 5 seconds or so or tapped on by finger for a few seconds, permitting the applied solution to be evenly spread inside the bottle and to prevent the seeds from sticking to the wet walls of the bottle. The bottle is placed back between rollers and is rotated at -60 rpm for an additional about 2 to about 5 minutes. The coating solution is thereby evenly coated on the seed surface. This resulted in a clear coating.

After the applied coating in the immediately above step visually appears dry or substantially dry, an additional 2 c.c. gellan gum solution was applied to the same 50 grams of corn seed by syringe into the syringe accessible end of the rotating bottle. This brought to which brings to 8 c.c. the amount of gellan gum solution applied.

Again, after this applied coating solution is applied, the bottle is then picked up by hand and shaken for about 2 to about 5 seconds or so or tapped on by finger for a few seconds, permitting the applied solution to be evenly spread inside the bottle and to prevent the seeds from sticking to the wet walls of the bottle. The bottle is placed back between rollers and rotates at about 60 rpm for an additional about 2 to about 5 minutes. The coating solution is thereby evenly coated on the seed surface.

After the applied coating in the above step visually appears dry an additional 2 c.c. gellan gum solution was applied to the same 50 grams of corn seed, whereby the total amount of gellan gum solution applied was 10 c.c.

After this applied coating solution is applied, the bottle is then picked up by hand and shaken for about 2 to about 5 seconds or so or tapped on by finger for a few seconds, permitting the applied solution to be evenly spread inside the bottle and to prevent the seeds from sticking to the wet walls of the bottle. The bottle is placed back between rollers and rotates at about 60 rpm for an additional about 2 to about 5 minutes. The coating solution is thereby evenly coated on the seed surface which resulted in a clear coating.

The coated seed is then poured out of the bottle and spread out for air drying. A visual inspection showed that an acceptable coated seed (corn) had been prepared which was illustrative of this invention.

FIG. 1. (UTC is untreated control corn seed; while the right hand side shows gellan gum coated corn seed. E=10 mls indicates the total amount of gellan gum composition applied).

This Example demonstrated that gellan gum applied as a clear aqueous coating in accordance with this invention is compatible with corn seed.

Example 2

Gellan Gum Coating on Corn Seed with Propylene Glycol

Purpose: To apply clear coat of gellan gum solution to corn seed to demonstrate that acceptable, protective seed coating can be obtained Method: Use a 1.5% Gellan solution prepared generally as described above.

|  | Weight (grams) |
|---|---|
| 1.5% Gellan | 21 |
| 0.10% sodium citrate** | 1.4 |
| 0.15% propylene glycol | 2.1 |
| 98.25% Deionized water | 1375.5 |

**Dihydrate, powder

The preparation and mixing of the gellan gum composition was carried out following the procedure of the previous Example except that the gellan gum composition here included propylene glycol, illustrative of a compatible plasticizer.

Seed Coating Procedure:

The procedure of adding gellan gum solution to seed in this Example followed in general the procedure of the Example above.

In each addition step of the five steps of addition of the gellan gum solution, about 2 c.c. of gellan gum solution was applied sequentially (as described above) to the same 50 grams of corn seed. Each such addition was followed by a mixing and rotating step of perhaps 2–5 minutes. The respective amounts of gellan gum solution added during and over five addition steps are:

TABLE 1

Gellan Gum Additions to Corn Seed

| Gellan Gum Added (c.c.) | Total Gellan Gum Added (c.c.) |
| --- | --- |
| 2 | 2 |
| 2 | 4 |
| 2 | 6 |
| 2 | 8 |
| 2 | 10 |

A visual inspection showed that acceptable seed coating was produced. This demonstrates that gellan gum with propylene glycol (illustrative of a plasticizer) applied as a clear aqueous coating in accordance with this invention is compatible with corn seed.

Example 3

Gellan Gum Coating with pigment: Red #40 Lake on corn seed (with HPMC) (HPMC=hydroxy propylmethyl cellulose)

Purpose: To apply color coat of gellan gum solution to corn seed to demonstrate that acceptable color seed coating can be obtained applying a gellan gum and HPMC in a seed coating.

Method: Using a 1.125% Gellan solution with 0.375% HPMC:

|  | Weight (grams) |
| --- | --- |
| 1.125% Gellan | 5.625 |
| 0.10% sodium citrate** | 0.50 |
| 0.375% HPMC | 1.875 |
| 98.4% Deionized water | 492 |

**Dihydrate, powder

Mixing Instructions: Follow Procedure Recited in Example 1

Color system added to 150 gram gellan/HPMC solution:

50 grams Red #40 Lake/H$_2$O

RED #40-Lake formulation: (% by weight)

26% Titanium dioxide

14% Red 40 cake

60% deionized water

Red #40 Lake was dispersed into a hot gellan gum/HPMC solution at 70° C.

Seed Coating Procedure: Generally follow procedure recited in Example 1

Corn seed used—50 grams; Five addition steps

TABLE 2

Gellan Gum Additions to Corn Seed

| Gellan Gum Added (c.c.) | Total Gellan Gum Added (c.c.) |
| --- | --- |
| 2 | 2 |
| 2 | 4 |
| 2 | 6 |
| 2 | 8 |
| 2 | 10 |

In this example, acceptable seed coating with color, was produced. This demonstrates that gellan gum with HPMC applied as a color aqueous coating in accordance with this invention is compatible with corn seed.

Example 4

Gellan Gum Coating with pigment: Red # 40 on soybean

Purpose: To apply a color coat of gellan gum solution to soybean to demonstrate that color gellan solution is compatible with more than one type of seed Method: Using a 1.5% Gellan solution with 0.15% propylene glycol in Example B Color system added to 150 grams of gellan solution:

Red #40 Lake having a composition as recited in the immediately previous Example, was dispersed into a hot gellan gum aqueous solution at 70 ° C.

Seed Coating Procedure: Follow generally the procedure recited in Example 1

Soybean used total 50 grams; five gellan gum composition addition steps

TABLE 3

Gellan Gum Additions to Soybean

| Gellan Gum Added (c.c.) | Total Gellan Gum Added (c.c.) |
| --- | --- |
| 2 | 2 |
| 2 | 4 |
| 2 | 6 |
| 2 | 8 |
| 2 | 10 |

In this example, acceptable color seed coating was produced. This demonstrates that color gellan gum solution applied as an aqueous color coating in accordance with this invention is compatible with more than one type of seed.

Example 5

Gellan Gum Coating with Red Color Dye on Sugar Beet Seed

Purpose: To apply a color coat of gellan gum solution to sugar beet seed to demonstrate that acceptable seed color coating can be obtained Method: Using a 1.5% Gellan solution with 0.15% propylene glycol Example 2

Color system added to 10 grams of gellan gum solution:

0.5 grams Red color dye solution

Red color dye has to be added into a hot gellan solution at 50° C.

Seed Coating Procedure: Follow procedure cited in Example 1

Sugar beet seed used total 25 grams; five addition steps

TABLE 4

Gellan Gum Additions to Sugar Beet

| Gellan Gum Added (c.c.) | Total Gellan Gum Added (c.c.) |
|---|---|
| 2 | 2 |
| 2 | 4 |
| 2 | 6 |
| 2 | 8 |
| 2 | 10 |

In this example, acceptable seed color coating were produced. This demonstrates that gellan gum solution applied as an aqueous color coating in accordance with this invention is compatible with more than one type of seed and produces an acceptable coated seed in accordance with this invention.

Example 6

Gellan Gum Coating on Corn Seed with Fungicide

Purpose: To apply clear coat of gellan gum solution with bioactive fungicide to corn seed to demonstrate that acceptable protective seed coating with bioactive materials can be obtained Method: Using a 1.5% Gellan solution prepared in Example 1

Add 0.858 mg of cyproconazole fungicide (96.3% active) into 1 c.c. ethanol in a 15 ml vial and shake gently until it is dissolved. Weigh 9 c.c. gellan gum solution into a 15 ml vial with 1 c.c. cyproconazole/ethanol solution and mix well.

Seed Coating Procedure: Follow generally the procedure cited in Example 1

Corn seed used total 50 grams; four addition steps

TABLE 5

Gellan Gum Additions to Corn Seed

| Gellan Gum Added (c.c.) | Total Gellan Gum Added (c.c.) |
|---|---|
| 2 | 2 |
| 2 | 4 |
| 2 | 6 |
| 2 | 8 |

In this example, acceptable, bioactive gellan gum seed coating was produced, and they demonstrate that gellan gum applied as a clear aqueous coating in accordance with-this invention is able to deliver bioactive fungicide to corn seed.

Example 7

Gellan Gum Coating on Corn Seed with a Bioactive (ammonium glyphosate) (herbicide)

Purpose: To apply a bioactive coat of gellan gum solution to corn seed to demonstrate that bioactives can be coated onto seed employing gellan seed coating.

Method: Prepare and use a 1.5% Gellan gum solution following generally the procedure of Example 1 and prepare and use a slurry of ammonium glyphosate (MON 8750). (MON 8750 is a registered trademark for commercial ammonium glyphosate made and sold by Monsanto Company, 800 North Lindbergh Blvd, St. Louis, Mo. 63167. ) MON 8750 is 87% wt. ammonium glyphosate.

A slurry of mono-ammonium glyphosate was prepared by slurrying MON 8750 with deionized water to form 43.5 wt. % composition based on mono-ammonium glyphosate.

Seed Coating Procedure:

Fifty grams of a selected seed type, such as corn and soybean, is weighed and poured into a 200 c.c. glass or plastic bottle container. The bottle is laid between two rollers and is rotated at a speed of about 60 rpm. This rotation proceeds for about a few minutes.

In a first part, an initial 2 c.c. of the above-described gellan coating solution is drawn into a syringe and the solution is applied from the syringe to the walls of the open-ended rotating bottle through a syringe accessible (open) end of the rotating bottle. After about one minute, about 0.22 c.c. of the above-described ammonium glyphosate composition was subsequently added via this syringe technique to the same seeds on top of the initial gellan gum coating.

After this coating solution is applied, the bottle is then picked up by hand from the rollers and shaken for about 2 to about 5 seconds or so or tapped on by finger for a few seconds, permitting the applied solution(s) to be evenly spread inside the bottle and to prevent seeds from sticking to the bottle walls. The bottle is placed back between rollers and rotates at -60 rpm for an additional about 2 to about 5 minutes. The solutions are thence applied evenly to the same 50 grams of corn seed inside the rotating bottle as a coating solution. The ammonium glyphosate is thereby coated on the gellan gum coated seed surface.

In a sequential part, after the seeds appeared visually dry or somewhat dry, an additional 2 c.c. of gellan gum solution is added via the syringe technique to the rotating bottle and after about one minute about 0.31 c.c. of ammonium glyphosate composition is likewise added. This is followed by picking up the bottle and shaking or tapping it, followed by a 2 to 5 minutes of rolling on the rollers.

After the seeds appeared dry or somewhat dry, an additional 2 c.c. of gellan gum composition was added by the above-described syringe technique followed by additional of 0.33 c.c. of ammonium glyphosate composition added also by the aforedescribed syringe technique. These addition steps were followed by picking up the bottle and shaking or tapping it, followed by about 2 to about 5 minutes of rolling on the aforedescribed rollers.

After the seeds appeared dry or somewhat dry, an additional 2 c.c. of gellan gum composition was added by the above-described syringe technique. These addition step was followed by picking up the bottle and shaking or tapping it, followed by about 2 to about 5 minutes or so of rolling on the rollers.

In this example, an acceptable, bioactive seed coating was produced. This example demonstrates that gellan gum applied as an aqueous seed coating in accordance with this invention can deliver bioactive materials including delivering more than one type of bioactive material.

Example 8

Gellan Gum Coating on Corn Seed with Glyphosate Isopropylamine

Purpose: To apply clear coat of gellan gum solution with bioactive glyphosate isopropylamine to corn seed to demonstrate that acceptable, protective seed coating with bioactive materials can be obtained Method: Using a 1.5% Gellan solution prepared in Example 1

Preparation of 1.5% gellan solution with 0.5% (active) glyphosate isopropylamine Add 10 c.c. of 46% AE glyphosate isopropylamine into 500 c.c. 1.5% hot gellan solution at 70° C. and mix thoroughly. The resulting solution is subsequently diluted to 0.5% glyphosate isopropylamine with 1.5% gellan solution Seed Coating Procedure: Follow generally the procedure recited in Example 1

Corn seed used total 50 grams; four additions:

TABLE 6

| Gellan Gum Added (c.c.) | Total Gellan Gum Added (c.c.) |
| --- | --- |
| 2 | 2 |
| 2 | 4 |
| 2 | 6 |
| 2 | 8 |

In this example, acceptable, bioactive seed coating was produced, and this demonstrates that gellan gum applied as a clear aqueous coating in accordance with this invention is able to deliver bioactive glyphosate isopropylamine to corn seed.

Example 9

Gellan Gum Coating on Corn Seed with Bioactive Glyphosate Acid

Purpose: To apply gellan gum solution with bioactive glyphosate acid to corn seed to demonstrate that acceptable, protective seed coating with bioactive materials can be obtained.

Method: Using a 1.5% Gellan solution prepared in Example 1

Using a 40.5% AE glyphosate acid slurry

Preparation of gellan/glyphosate acid solution: Add 10 ml of glyphosate acid slurry to 90 ml of hot 1.5% gellan solution and mix thoroughly Seed Coating Procedure: Follow procedure cited in Example 1

Finish with about 0.8% weight glyphosate acid on seed.

Corn seed used total 50 grams.

TABLE 7

| Gellan Gum Added (c.c.) | Total Gellan Gum Added (c.c.) |
| --- | --- |
| 2 | 2 |
| 2 | 4 |
| 2 | 6 |
| 2 | 8 |
| 2 | 10 |

In this example, acceptable, bioactive seed coating was produced, and this demonstrates that gellan gum applied as an aqueous coating in accordance with this invention is able to deliver bioactive glyphosate acid to corn seed.

Thus, it is apparent that there has been provided, in accordance with the instant invention, a product and process that fully satisfies the objects and advantages set forth herein above. While the invention has been described with respect to various specific examples and embodiments thereof, it is understood that the invention is not limited thereto and many alternatives, modifications and variations will be apparent to those skilled in the art in light of the foregoing description. Accordingly, it is intended to embrace all such alternatives, modifications and variations as fall within the spirit and broad scope of the invention.

What is claimed is:

1. A process for preparing a coated seed which process comprises:
   a. admixing gellan gum, a pesticide, and water under shear to prepare an aqueous coating composition useful for coating a seed; and
   b. applying the aqueous coating composition in an adherent fashion to a seed whereby said coated seed is formed and, optionally, drying said seed to form a dried coated seed;

wherein the aqueous coating composition comprises gellan gum in an amount from about 0.1% to about 10% by weight of the total weight of the aqueous composition and wherein the viscosity of the aqueous coating composition is from about 44 cps to about 55,000 cps.

2. The process of claim 1 wherein the aqueous coating composition comprises gellan gum in an amount from about 0.25% to about 5% by weight of the total weight of the aqueous composition.

3. A seed produced by the process of claim 2.

4. The process of claim 1 wherein the pesticide is a herbicide or a fungicide.

5. The process of claim 1 wherein the pesticide is a glyphosphate-based herbicide.

6. The process of claim 5 wherein the glyphosphate-based herbicide is the ammonium salt, the trimethylsulfonium salt or the isopropylammonium salt of glyphosate.

7. The process of claim 1 wherein the viscosity of the aqueous coating composition is from about 2,200 cps to about 50,000 cps.

8. The process of claim 1 wherein the aqueous coating composition comprises from about 0.75% to about 3% by weight of the total weight of the aqueous composition.

9. A seed produced by the process of claim 1.

10. A process for preparing a coated seed which process comprises:
    a. admixing gellan gum, a pesticide, and water under shear to prepare an aqueous coating composition useful for coating a seed; and
    b. applying the aqueous coating composition in an adherent fashion to a seed whereby said coated seed is formed and, optionally, drying said seed to form a dried coated seed;

wherein the viscosity of the aqueous coating composition is from about 44 cps to about 55,000 cps.

11. The process of claim 10 wherein the pesticide is a herbicide or a fungicide.

12. A seed produced by the process of claim 11.

13. The process of claim 10 wherein the pesticide is a glyphosphate-based herbicide.

14. The process of claim 13 wherein the glyphosphate-based herbicide is the ammonium salt, the trimethylsulfonium salt or the isopropylammonium salt of glyphosate.

15. The process of claim 10 wherein the viscosity of the aqueous coating composition is from about 2,200 cps to about 50,000 cps.

16. A seed produced by the process of claim 10.

* * * * *